US011607467B2

(12) United States Patent
Kulaga

(10) Patent No.: US 11,607,467 B2
(45) Date of Patent: Mar. 21, 2023

(54) SYNTHESIS OF NANOPARTICLE IN LIQUID, SEMI-SOLID MEDIA AND IN CELLS AND TISSUES USING COLD PLASMA TECHNOLOGY

(71) Applicant: Plasmology4, Inc., Scottsdale, AZ (US)

(72) Inventor: Emilia M. Kulaga, Scottsdale, AZ (US)

(73) Assignee: PLASMOLOGY4, INC., Scottsdale, AZ (US)

( * ) Notice: Subject to any disclaimer, the term of this patent is extended or adjusted under 35 U.S.C. 154(b) by 0 days.

(21) Appl. No.: 15/611,098

(22) Filed: Jun. 1, 2017

(65) Prior Publication Data

US 2018/0050120 A1 Feb. 22, 2018

Related U.S. Application Data

(60) Provisional application No. 62/346,425, filed on Jun. 6, 2016.

(51) Int. Cl.
| | |
|---|---|
| A61L 2/00 | (2006.01) |
| A61K 41/00 | (2020.01) |
| A61L 2/18 | (2006.01) |
| A61K 33/00 | (2006.01) |
| A61L 2/14 | (2006.01) |
| A61K 33/243 | (2019.01) |
| A61K 33/242 | (2019.01) |
| A01N 59/16 | (2006.01) |
| A01N 59/20 | (2006.01) |
| A61K 33/24 | (2019.01) |
| A61K 33/34 | (2006.01) |
| A61K 33/38 | (2006.01) |
| A61N 1/44 | (2006.01) |
| B22F 1/07 | (2022.01) |
| B22F 9/14 | (2006.01) |
| H05H 1/46 | (2006.01) |

(52) U.S. Cl.
CPC .......... *A61L 2/0011* (2013.01); *A01N 59/16* (2013.01); *A01N 59/20* (2013.01); *A61K 33/00* (2013.01); *A61K 33/24* (2013.01); *A61K 33/242* (2019.01); *A61K 33/243* (2019.01); *A61K 33/34* (2013.01); *A61K 33/38* (2013.01); *A61K 41/00* (2013.01); *A61K 41/0052* (2013.01); *A61L 2/0082* (2013.01); *A61L 2/14* (2013.01); *A61L 2/18* (2013.01); *A61N 1/44* (2013.01); *B22F 1/07* (2022.01); *B22F 9/14* (2013.01); *B22F 2202/13* (2013.01); *H05H 1/46* (2013.01); *H05H 2242/20* (2021.05); *H05H 2245/50* (2021.05)

(58) Field of Classification Search
None
See application file for complete search history.

(56) References Cited

U.S. PATENT DOCUMENTS

| | | | |
|---|---|---|---|
| 7,633,231 B2 | 12/2009 | Watson | |
| 8,005,548 B2 | 8/2011 | Watson | |
| 8,810,134 B2 | 8/2014 | Watson | |
| 8,928,230 B2 | 1/2015 | Watson et al. | |
| 9,006,976 B2 | 4/2015 | Watson et al. | |
| 9,437,401 B2 | 9/2016 | Watson et al. | |
| 9,521,736 B2* | 12/2016 | Jacofsky | A61N 1/44 |
| 2005/0003019 A1* | 1/2005 | Petersen | A01N 59/16 |
| | | | 424/617 |
| 2012/0107369 A1* | 5/2012 | Yeoman, III | A61L 27/52 |
| | | | 977/906 |
| 2014/0188071 A1 | 7/2014 | Jacofsky et al. | |
| 2014/0188097 A1 | 7/2014 | Watson et al. | |
| 2016/0089545 A1 | 3/2016 | Juluri et al. | |
| 2016/0106993 A1* | 4/2016 | Watson | H01J 37/32825 |
| | | | 604/23 |
| 2017/0246468 A1* | 8/2017 | Kalghatgi | A61N 1/44 |

FOREIGN PATENT DOCUMENTS

| | | | | |
|---|---|---|---|---|
| JP | 2014043381 A | 3/2014 | | |
| WO | 2004059027 A2 | 7/2004 | | |
| WO | 20100068985 A1 | 6/2010 | | |
| WO | 2012083442 A1 | 6/2012 | | |
| WO | WO-2012083442 A1 * | 6/2012 | ......... | A61K 49/1863 |

OTHER PUBLICATIONS

Cheng et al (Synergistic effect of gold nanoparticles and cold plasma on glioblastoma cancer therapy. J. Phys. D: Appl. Phys. 47 (2014) 335402. p. 1-8) (Year: 2014).*
Nagahiro (JP2014043381 machine translation) (Year: 2014).*
Wikipedia (https://en.wikipedia.org/wiki/Biofilm (downloaded on May 21, 2022). (Year: 2022).*
PCT International Search Report & Written Opinion for PCT Application No. PCT/US2017/036177 dated Oct. 13, 2017; 16 Pages.
Vladimir Scholtz et al.; "Nonthermal Plasma—A Tool for Decontamination and Disinfection", Biotechnology Advances, Jan. 1, 2015, XP055185650, 10.1016/m.biotechadv.2015.01.002.
Xiaoqian Cheng et al., Cold Plasma Accelerates the Uptake of Gold Nanoparticles Into Glioblastoma Cells, Plasma Process. Polym. 2015, 12, 1364-1369, 2015.
Xiaoqian Cheng et al., Synergistic effect of gold nanoparticles and cold plasma on glioblastoma cancer therapy, Journal of Physics D: Applied Physics, 2014 IOP Publishing Ltd.

* cited by examiner

*Primary Examiner* — Jake M Vu
(74) *Attorney, Agent, or Firm* — Ballard Spahr LLP

(57) ABSTRACT

A method of forming metal nanoparticles includes applying a substance to an area of interest, applying cold plasma to the area of interest, and synthesizing nanoparticles from the substance using the cold plasma in the area of interest, wherein the substance is a solution that contains metal ions, and the nanoparticles synthesized are metallic in nature.

9 Claims, 4 Drawing Sheets

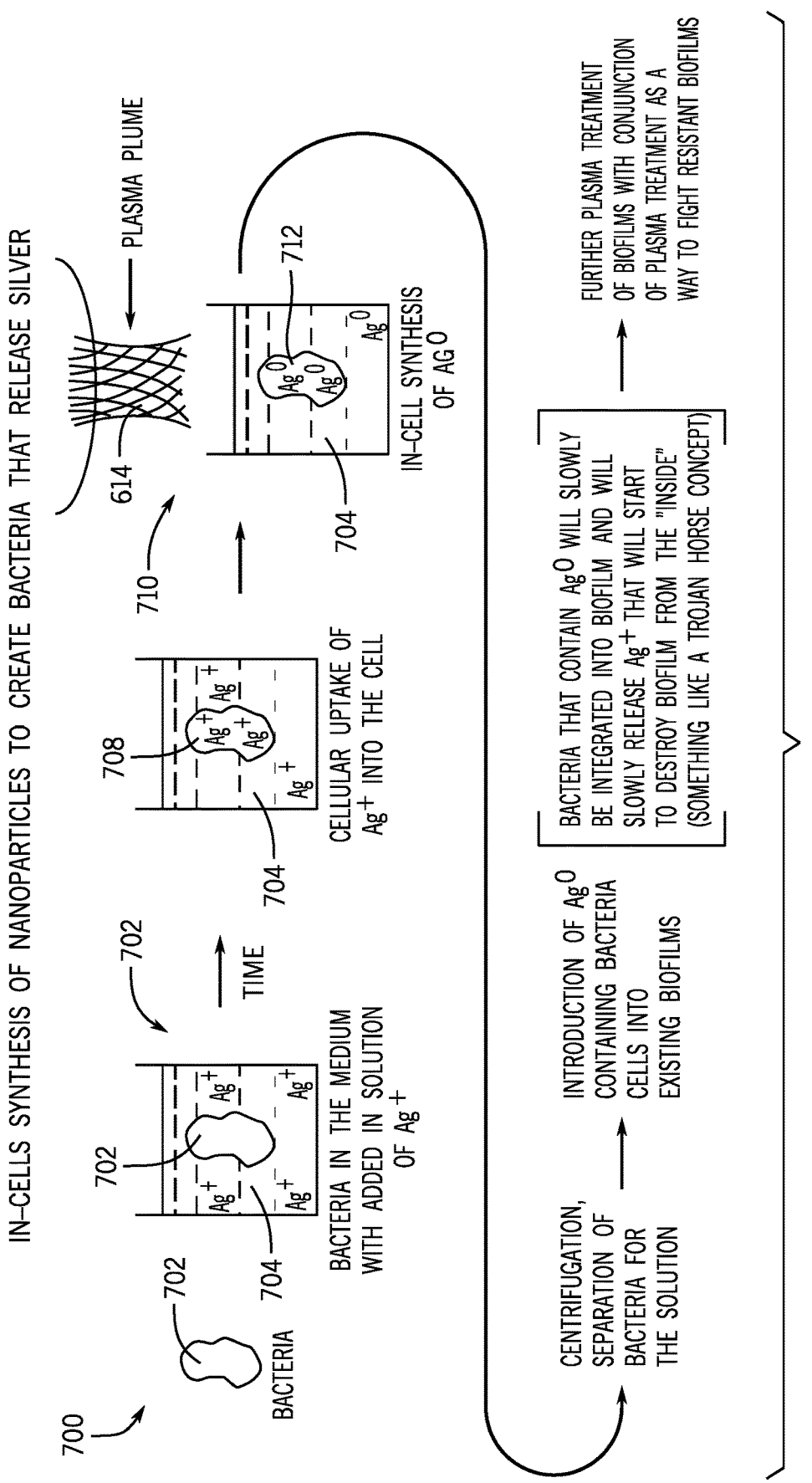

SYNTHESIS OF NANOPARTICLE IN LIQUID, SEMI-SOLID MEDIA AND IN CELLS AND TISSUES USING COLD PLASMA TECHNOLOGY

CROSS-REFERENCE TO RELATED APPLICATIONS

This application claims priority to and benefit of U.S. Provisional Application No. 62/346,425 entitled "SYNTHESIS OF NANOPARTICLE IN LIQUID, SEMI-SOLID MEDIA AND IN CELLS USING COLD PLASMA TECHNOLOGY," filed on Jun. 6, 2016, which is hereby incorporated by reference in its entirety.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Modern medicine enables physicians to treat a wide variety of wounds and infections on a patient. For example, physicians may treat these wounds and infections using topical medication (e.g., creams, foams, gels, ointments, bandages, etc.) and/or internal medication (e.g., medicine administered orally, intravenously). Unfortunately, existing treatments may be costly, ineffective, and/or slow to treat certain wounds and infections.

BRIEF DESCRIPTION OF THE DRAWINGS

Various features, aspects, and advantages of the present invention will become better understood when the following detailed description is read with reference to the accompanying figures in which like characters represent like parts throughout the figures, wherein:

FIG. 4 is a flow diagram illustrating an embodiment of a method for using cold plasma to synthesize Ag nanoparticles inside cells and tissues.

DETAILED DESCRIPTION OF SPECIFIC EMBODIMENTS

Figure 1:
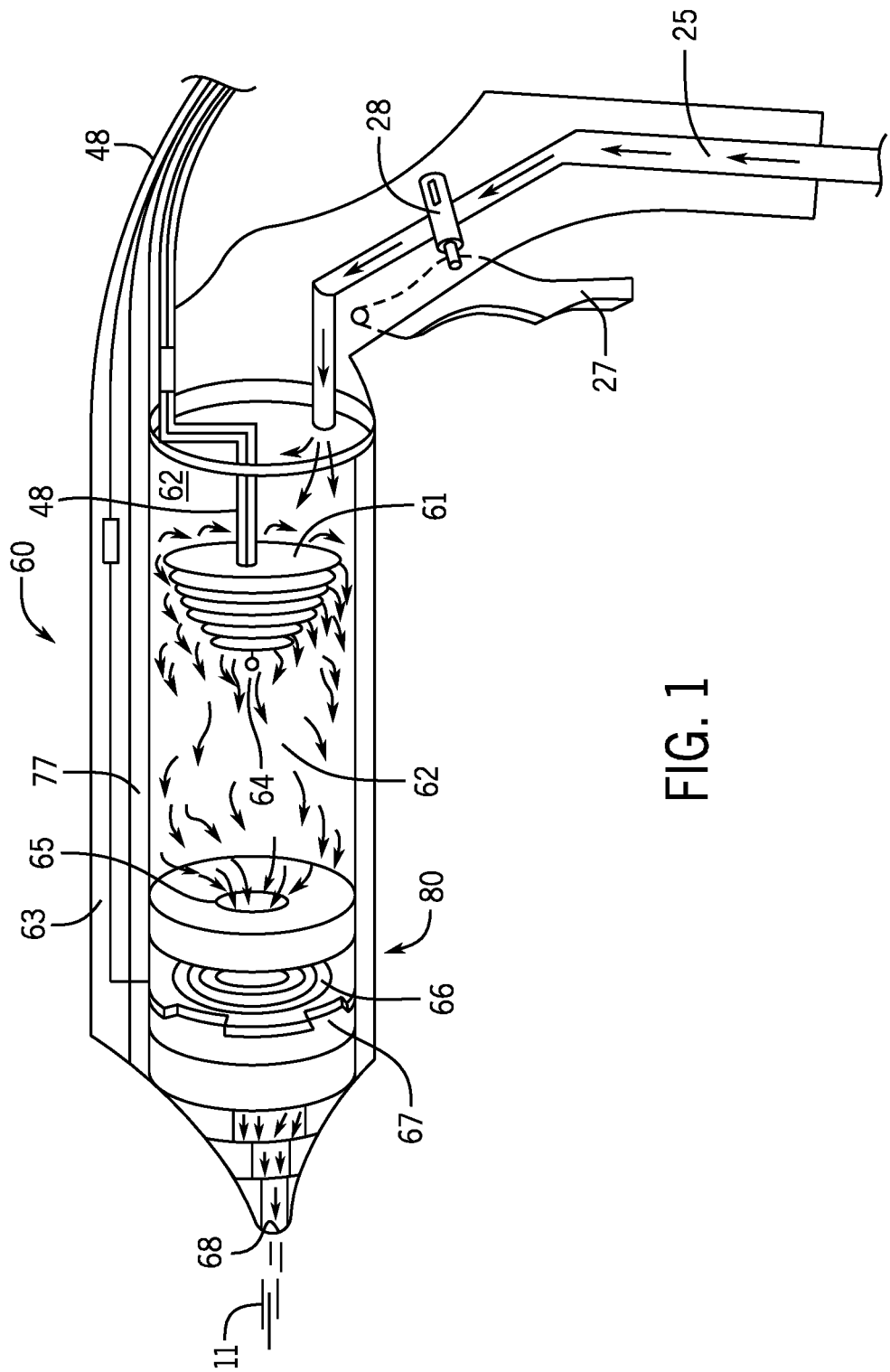
FIG. 1 is a cutaway view of an embodiment of a hand-held cold plasma device.

One or more specific embodiments of the present invention will be described below. These described embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present application may employ any suitable technique for generating cold plasma, such as described in detail below and/or described in any of the following patents or patent applications as non-limiting examples, to facilitate synthesis of nanoparticles. Accordingly, a variety of alternative techniques may be used for generating cold plasma within the scope of the present application. The nanoparticles may be synthesized using cold plasma in any suitable application, such as but not limited to medical treatment.

The present application incorporates by reference in its entirety U.S. Pat. No. 7,633,231 B2, entitled "Harmonic Cold Plasma Device and Associated Methods" and issued on Dec. 15, 2009.

The present application incorporates by reference in its entirety U.S. Pat. No. 8,005,548 B2, entitled "Harmonic Cold Plasma Device and Associated Methods" and issued on Aug. 23, 2011.

The present application incorporates by reference in its entirety U.S. Pat. No. 8,810,134 B2, entitled "Harmonic Cold Plasma Device and Associated Methods" and issued on Aug. 19, 2014.

The present application incorporates by reference in its entirety U.S. Pat. No. 9,006,976 B2, entitled "Cold Plasma Treatment Devices and Associated Methods" and issued on Apr. 14, 2015.

The present application incorporates by reference in its entirety U.S. Pat. No. 8,928,230 B2, entitled "Cold Plasma Treatment Devices and Associated Methods" and issued on Jan. 6, 2015.

The present application incorporates by reference in its entirety U.S. patent application Ser. No. 14/145,898, entitled "Method and Apparatus for Dielectric Barrier Discharge Wand Cold Plasma Device" and filed on Dec. 31, 2013.

The present application incorporates by reference in its entirety U.S. patent application Ser. No. 14/575,791, entitled "System and Method for Plasma Treatment Using Directional Dielectric Barrier Discharge Energy System" and filed on Dec. 18, 2014.

The present application incorporates by reference in its entirety a document entitled "Synthesis of Nanoparticles in Liquid, Semi-Solid media and in cells using Cold Plasma Technology", which is attached hereto as an Appendix.

A variety of nanoparticles (e.g., silver, gold, copper, and/or other metals) may be used for medical treatments, such as for killing disease-causing and/or infection-causing bacteria, or the treatment or diagnostic of malignant cells and masses. Nanoparticles may be applied in topical treatments (e.g., treatments used on an exterior of a patient's body), internal treatment (e.g., surgery), or systemically (e.g. intravenous). Unfortunately, synthesis of nanoparticles may be costly and involves additional safety precautions (e.g., environmental safety). In addition, it may be challenging and expensive to keep nanoparticles well dispersed and to reduce nanoparticle aggregation or agglomeration.

The disclosed embodiments include systems and methods for using cold plasma technology to synthesize silver (Ag) nanoparticles or other metal nanoparticles (e.g., gold, copper) inside cells, biological tissues, skin layers or liquid media, in vitro and in vivo. In addition, the disclosed embodiments include synthesizing Ag or other metal nanoparticles in-situ to application of a cold plasma system (e.g., to treat diseased or infected areas). For example, Ag nanoparticles may be synthesized concurrent with application of the cold plasma system such that Ag nanoparticles created in the tissue may release silver ions ($Ag^+$) to help kill bacteria while the cold plasma may add in the bactericidal effects to speed up tissue healing and decrease levels of infection.

In certain embodiments, the cold plasma system discussed herein may include a device (e.g., cold plasma applicator, tool, or apparatus) capable of providing streaming atmospheric pressure cold plasma inside a hand-held unit without the use of a negative electrode configuration. The device is capable of discharging cold plasma (preferably 65-99° F.) into ambient aft with simultaneously different radio frequency (RF) wavelengths and their harmonics. The device comprises a RF tuning network that is powered by a low-voltage power supply connected to a series of high-voltage cons and capacitors that are networked to produce a 150-kV dielectric RF signal. The RF energy signal is transferred to the cold plasma device through a protected cable that allows the electrical energy to be transferred without any substantial corona discharge energy loss. The RF energy signal is transferred to a housing having an interior space defined by a wall, and dispersed through an electrode comprising a plurality of plates positioned in substantially parallel, spaced-apart fashion within the inner space. The electrode plates are supported by a support rod that is in signal communication with a source of RF energy. The rod extends through each of the plates and supports a distance therebetween. A surface area of an upstream plate is greater than a surface area of a downstream plate, and the plates have various thicknesses to create multiple frequencies.

Helium, or any working feed gas can be introduced into the inner space upstream of the plates, where electron separation is initiated. The energized gas flows downstream into a magnetic compression chamber, comprising a first toroidal magnet having a first alignment positioned within the inner space downstream of the plates and a second toroidal magnet having a second alignment opposite the first alignment positioned within the inner space downstream of the first magnet. The first and the second magnets are substantially parallel and coaxial, and each has a central orifice.

A support is positioned between the first and the second magnet, the support having an aperture therethrough. Affixed to the support is an induction grid in frequency harmony with the electrode. The grid comprises a central capacitance element placeable in electrical communication with a source of power and a plurality of metal rods, each having a capacitance element affixed at opposed ends. The rods are approximately symmetrically arrayed about the central capacitance element, two outermost metal rods placeable in electrical communication with the power source.

In this device gas entering the inner space is energized by the electrode, is channeled through the first magnet orifice, and contacts the grid to further energize the gas and create a multiple-frequency cold plasma thereby. A balanced frequency network grid with capacitance creates the final electron separation, which is inverted magnetically and exits out the housing through an orifice with a nozzle. The cold plasma thus generated has been shown to be capable of facilitating and accelerating a healing process in flesh wounds on animal laboratory specimens, and to kill bacteria in vitro. With this in mind, FIG. 1 shows a cutaway view of an embodiment of a hand-held cold plasma device 60 (e.g., cold plasma applicator, tool, or apparatus). The embodiment of FIG. 1 is merely one possible configuration of a cold plasma device 60 that may be used to facilitate synthesis of nanoparticles. Accordingly, a variety of alternative cold plasma devices also may be used to generate cold plasma to facilitate synthesis of nanoparticles within the scope of the present application. The hand-held device 60 is configured to produce multiple-frequency cold plasma 11 without the use of internal ground electrodes. The hand-held device 60 may be coupled to a RF power feed 48, and a gas port 25. The gas port 25 is configured to supply gas flow controlled with a trigger 27, which is connected in operative relation to a gas flow valve 28. The hand-held device 60 may include a plurality of plates 61 (e.g., 2, 3, 4, 5, 6, 7, 8, 9, 10, or more plates) that comprise non-insulated nickel-plated discs having decreasing diameters from the proximal to the distal end of the stack. The plates 61 are positioned within a first chamber 62 within a housing 63. The generated cold plasma 64 passes into a second chamber 80 containing a first, north magnet 65, a harmonic ring system 66, and a second, south magnet 67 before passing out the orifice 68.

Figure 2:
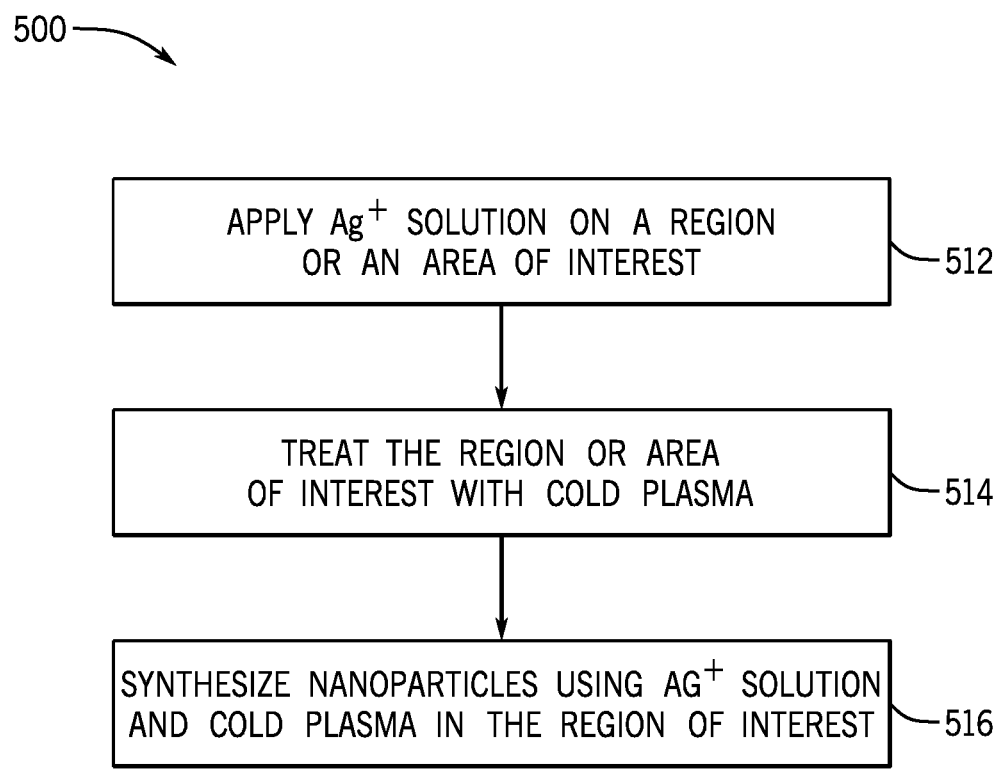
FIG. 2 is a flow chart illustrating an embodiment of a method for using cold plasma to synthesize silver (Ag) nanoparticles.

It may be appreciated that any one or more or a combination of the embodiments described above and embodiments incorporated by reference may be used to synthesize nanoparticles concurrent with cold plasma medical treatment as discussed in further detail below. In other words, the present application is not intended to be limited to any particular configuration of a cold plasma device. FIG. 2 is a flow chart illustrating an embodiment of a method 500 for simultaneous cold plasma and nanoparticle medical treatment, wherein the cold plasma helps to synthesize nanoparticles (e.g., cold plasma generated via the cold plasma device 60 set forth above). Although the illustrated embodiments of the method 500 are directed to synthesizing Ag nanoparticles, a substantially similar method (e.g., with appropriate metal ion solutions) may be used to synthesize other metal nanoparticles such as gold (Au) nanoparticles, platinum (Pt), and copper (Cu) nanoparticles, etc. The method 500 includes applying $Ag^+$ solution (e.g., $AgNO_3$) on a region or an area of interest (step 512), and treating the region or area of interest with cold plasma (step 514). The $Ag^+$ solution (e.g., $AgNO_3$) may be applied to or deposited on the region or area of interest by a mist, moist cotton, dressing, pad, tube, pipette, etc. Also bandages that contain silver can provide a source of silver ions. The region or area of interest may be an external tissue (e.g., skin), wound or an internal tissue (e.g., tissue within a cavity of a patient's body or internal tissue being exposed during a surgical operation). Furthermore, the region or area of interest may be biological tissue or cells. The region or area of interest may also be a media such as gel, hydrogel, or liquid, in vivo or in vitro. Upon the application of the $Ag^+$ solution, the $Ag^+$ solution is absorbed into the region or area of interest. It may be appreciated that the distribution of the $Ag^+$ ions may be rather dispersed and uniform. It may also be appreciated that the $Ag^+$ ions may settle in pores of the skin or tissue or settled in-between cells such that the $Ag^+$ ions are unlikely to aggregate or agglomerate (e.g., separated by pores and/or cells).

The method 500 also includes treating the region or area of interest with cold plasma (step 514). Upon the completion of the step 512 set forth above, the region or area of interest is treated with cold plasma (e.g., generated using the cold plasma device 60 set forth above) (step 514). Finally, the method 500 includes synthesizing nanoparticles using the $Ag^+$ solution and the cold plasma in the region or area of interest (step 516). While the region or area of interest is exposed to cold plasma, the $Ag^+$ ions may be reduced to Ag atom (e.g., $Ag^0$) by gaining electrons introduced by the cold plasma (e.g., $Ag^+$ (aq)+$e^- \rightarrow Ag^0$ (s), wherein "aq" denotes aqueous state and "s" denotes solid state), or generated through the process of application of plasma inside or outside the cells [from the interaction of plasma with the cell structures]. As the treatment or application of the cold plasma proceeds, more $Ag^+$ ions are reduced to $Ag^0$ atoms, leading to formation of Ag nanoparticles. Because the initial distribution of the $Ag^+$ ions are rather dispersed for reasons set forth above, the distribution of the Ag nanoparticles may also be dispersed (e.g., separated by tissue's or skin's pores, or cells), which may significantly reduce the chance of particle aggregation or agglomeration. Noted that the characteristics of the Ag nanoparticle formation (e.g., particle size, distribution, concentration, separation distance) may be tailored by varying the initial solution concentration, time of exposure, distance of the plasma device 60 (e.g., cold plasma plume length) and/or varying the plasma-generating electrical signal (e.g., change power, amplitude, frequency/frequencies, pulse timing). Method 500 may be repeated at appropriate intervals (e.g. seconds, minutes, hours, days, weeks, months, years) until a desired outcome is obtained.

The Ag nanoparticles created in the region or area of interest will release $Ag^+$ to help kill bacteria, algae, fungi, etc. in vitro or in vivo (e.g., oligodynamic effects or bactericidal effects). In addition, since the Ag nanoparticles are created in-situ with the application of cold plasma, the cold plasma may also add in the bactericidal effects, and may speed up healing of tissues, decrease levels of infection significantly, and substantially reduce or inhibit biofilm formation or aid in killing of the biofilm or hindering the biofilm formation or weakening the biofilm resistance to other insults which may be of chemical means, pharmacologic means, electrical means or body immune system mechanisms (e.g., bacteria cells stick to each other and often these bacteria cells adhere to a surface, resulting in the formation of a biofilm). Furthermore, with the disclosed embodiments above, it may be possible to use a low concentration of $Ag^+$ ions to synthesize Ag nanoparticles as to reduce the amount of Ag nanoparticles usage. With the disclosed embodiments above, it may also be possible to reduce the chance of Ag nanoparticle aggregation or agglomeration, thus avoid the issues of cytotoxicity. Additionally, the usage of Ag created through plasma application will prevent growth of biofilm.

Figure 3:
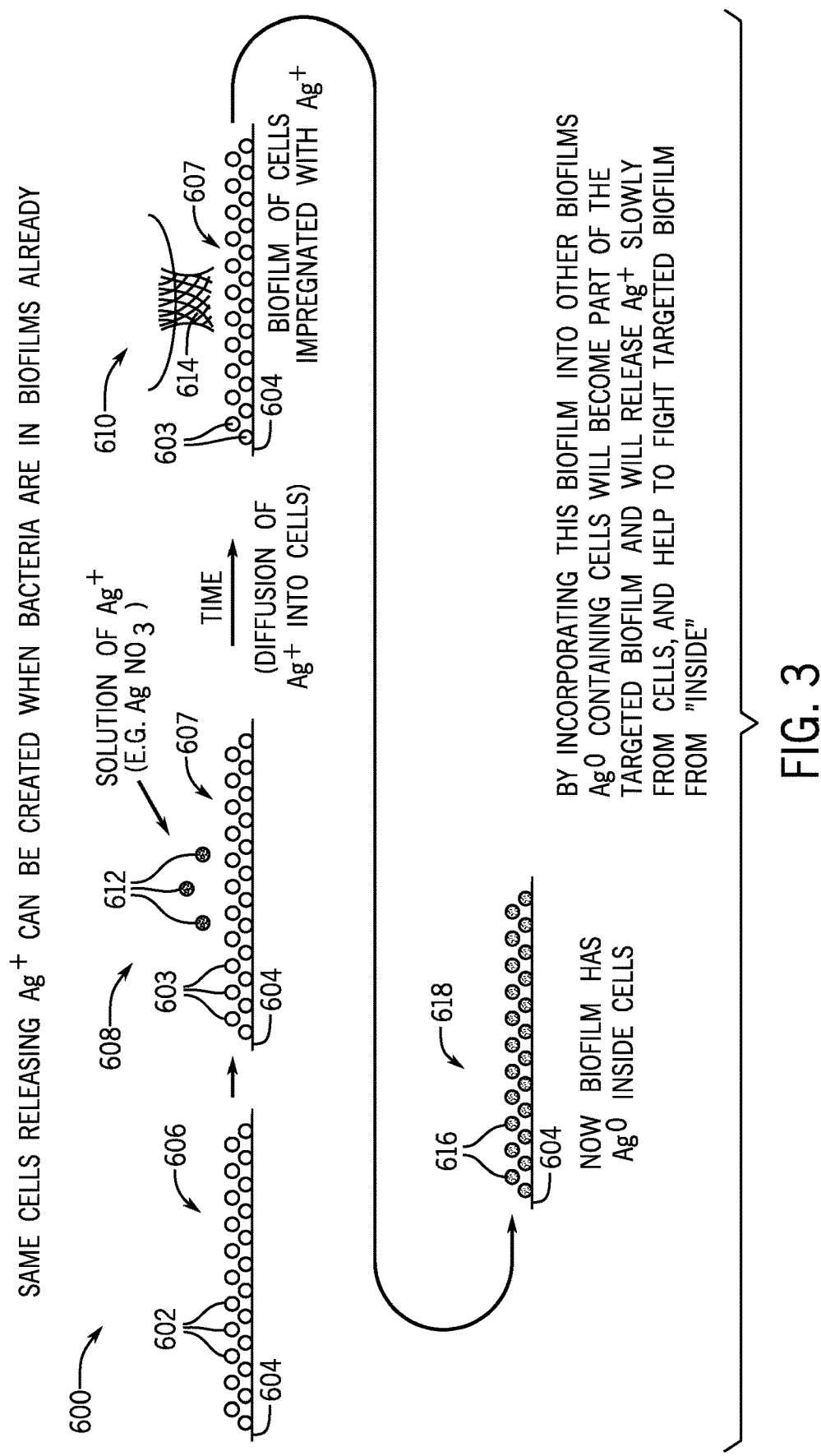
FIG. 3 is a flow diagram illustrating an embodiment of a method for using cold plasma to synthesize Ag nanoparticles inside a biofilm.

In particular, the method 500 may be used to synthesize Ag nanoparticles inside of cells and/or in a biofilm matrix or biofilm matrix (e.g., a biofilm formed by bacteria cells). FIG. 3 is a flow diagram illustrating an embodiment of a method 600 for synthesizing Ag nanoparticles inside a biofilm or biofilms. In the illustrated embodiment, bacteria cells or cells 602 stick together and may have adhered to a surface 604, forming a biofilm 606, wherein the surface 604 may be an external surface (e.g., skin) or an internal surface (e.g., inside a cavity of the patient's body). In step 608, the $Ag^+$ solution (e.g., $AgNO_3$) 612 is applied to the biofilm 606. With time, the $Ag^+$ ions diffuse into the biofilm and the cells 602 such that the cells 602 are impregnated with $Ag^+$ ions, resulting in $Ag^+$ impregnated cells 603 and $Ag^+$ impregnated biofilm matrix 607. In step 610, cold plasma (e.g., cold plasma plume) 614 is generated (e.g., via a dielectric barrier discharge or DBD energy system, a cold plasma applicator, or the hand-held cold plasma device 60) to treat the biofilm 606, 607 (e.g., the $Ag^+$ impregnated cells 603) so as to reduce these impregnated $Ag^+$ ions into $Ag^0$ atoms. As such, Ag nanoparticles are synthesized inside and impregnated within the biofilm 606, 607, resulting in $Ag^0$ impregnated cells 616 and an Ag nanoparticle impregnated biofilm 618. It may be appreciated that by incorporating the Ag nanoparticle impregnated biofilm 618 into another biofilm (e.g., a targeted biofilm, different from the biofilm 606), the $Ag^0$ impregnated cells 616 may be actively incorporated into the targeted biofilm and may release $Ag^+$ ions slowly from the $Ag^0$ impregnated cells 616 (e.g., of the Ag nanoparticle impregnated biofilm 618). As such, the Ag nanoparticle impregnated biofilm 618 created using cold plasma disclosed herein may help to fight and kill the targeted biofilm from inside and/or hinder the growth of the targeted biofilm.

In another embodiment, the method 500 may be used to synthesize Ag nanoparticles inside bacteria and/or fungi cells to create cells that release $Ag^+$. FIG. 4 is a flow diagram illustrating an embodiment of a method 700 for synthesizing Ag nanoparticles inside bacteria cells. In the illustrated embodiment, bacteria 702 may be placed in a medium 704 containing $Ag^+$ solution (e.g., $AgNO_3$) (step 706). With time, $Ag^+$ ions diffuse inside the bacteria 702 (e.g., cellular uptake of $Ag^+$ into the cell), forming $Ag^+$ impregnated bacteria 708. In step 710, cold plasma (e.g., cold plasma plume) 614 is generated (e.g., via the DBD energy system 10 or the cold plasma applicator 214) to treat the $Ag^+$ impregnated bacteria 708 so as to reduce these impregnated $Ag^+$ ions into $Ag^0$ atoms. As such, Ag nanoparticles are synthesized inside and impregnated with the bacteria, resulting in $Ag^0$ impregnated bacteria 712. It may be appreciated that the $Ag^0$ impregnated bacteria 712 may be separated from the solution 704 (e.g., via centrifugation), and the $Ag^0$ impregnated bacteria 712 may be introduced into a biofilm (e.g., targeted biofilm). The $Ag^0$ impregnated bacteria 712 may be slowly integrated into the targeted biofilm and may slowly release $Ag^+$ ions that may in turn destroy the targeted biofilm (e.g., from inside, similar to a Trojan horse concept). Additionally, the cold plasma treatment in conjunction with the incorporation of the $Ag^0$ impregnated bacteria 712 may assist fighting or killing the targeted biofilm or hindering the growth of the targeted biofilm.

The bacteria 702 may be a non-pathogenic strain of bacteria, and the $Ag^0$ impregnated non-pathogenic strain of bacteria 712 may be introduced into a pathogenic biofilm. In certain embodiments, the bacteria 702 may be a non-antibiotic resistant strain of bacteria. The $Ag^0$ impregnated non-antibiotic resistant strain of bacteria 712 may be introduced into an antibiotic resistant biofilm such that a portion of the antibiotic resistant bacteria is replaced by non-resistant, $Ag^+$ eluting bacteria. And the synthesis of Ag in tissues, implants to prevent the growth of biofilm. In the same way nanoparticles can be synthesized using plasma on tissues, where there is a probability of infection (e.g. surgical site). Synthesized nanoparticles together with plasma application will prevent bacterial colonization or biofilm growth.

In one embodiment, the method 500 may be used for synthesizing metal nanoparticles (e.g., Ag, Au, Pt, or Cu particles) in a media such as liquid (e.g., water). In another embodiment, the method 500 may be used for synthesizing nanoparticles of Ag, Au, Pt, or Cu in cancerous cells. In particular, such embodiment may help in cancer imaging. For example, during a surgery (e.g., to remove a tumor), the ion containing solution (e.g., $Au^+$ solution) may be applied (e.g., sprayed or poured) onto the surgical region or area so as to allow the ions to diffuse into the tissue and/or cells. As appreciated, cellular uptake of ions, particles, drugs, etc. of cancerous cells is faster than that of healthy cells. Once the ions are inside the tissue and/or cells, cold plasma may be generated (e.g., via the cold plasma device 60) to synthesize metallic nanoparticles inside the tissue and/or cells. It may be appreciated that the uptake of $Ag^+$, $Au^+$, $Pt^+$, $Cu^+$, or $Cu^{2+}$ ions inside the tissue and/or cells may also enable diagnostic possibilities to see cancer cells (e.g., with magnetic resonance), and better visualization of tumor margins. Once the nanoparticles are synthesized inside the tissue and/or cells, further application of cold plasma may induce local heating of the tissue and/or cells due to RF energy absorbing nanoparticles. In other words, the RF induced local heating of the metallic nanoparticles containing tissue and/or cells may be used as an anticancer therapy.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method, comprising:
applying a substance to an area of interest, wherein the area of interest comprises a biofilm, wherein cells adhere to skin to form the biofilm, wherein the substance is a solution that contains metal ions, wherein the metal ions of the substance diffuse into the area of interest, and wherein the metal ions impregnate the cells within the biofilm;
subsequent to diffusion of the metal ions into the area of interest and impregnation of the cells of the biofilm with the metal ions, applying cold plasma to the area of interest; and
with at least a portion of the applied cold plasma within the area of interest, synthesizing nanoparticles inside cells within the biofilm, wherein the nanoparticles synthesized are metallic in nature, and wherein the nanoparticles are synthesized when the cold plasma within the area of interest reduces the metal ions impregnated within cells within the biofilm to metal atoms such that the cells contain the metal atoms,
wherein following reduction of the metal ions impregnated within the cells within the biofilm to metal atoms such that the cells contain the metal atoms, the biofilm is incorporated into a second, targeted biofilm that is different from the biofilm.

2. The method of claim 1, wherein the metal ions comprise silver ions ($Ag^+$), gold ions ($Au^+$), copper ions ($Cu^+$ and/or $Cu^{2+}$), platinum ions ($Pt^+$), or a combination thereof.

3. The method of claim 1, further comprising:
applying additional cold plasma to the area of interest to heat the synthesized nanoparticles to provide local heating to the area of interest.

4. The method of claim 1, wherein the cold plasma is generated using a hand-held device.

5. The method of claim 1, wherein the cells that form the biofilm are bacteria cells, wherein the biofilm further comprises matrix, and wherein the metal ions impregnate the bacteria cells.

6. The method of claim 5, wherein the metal ions impregnate the matrix.

7. The method of claim 1, wherein the metal ions impregnate the cells through cellular uptake.

8. The method of claim 7, wherein the metal ions comprise silver ions ($Ag^+$), wherein the metal atoms comprise silver atoms($Ag^0$), and wherein following reduction of the silver ions to silver atoms, cells containing the silver atoms release silver ions.

9. The method of claim 1, wherein following incorporation of the biofilm into the second, targeted biofilm, the cells release metal ions.

* * * * *